US011105823B2

United States Patent
Dennis et al.

(10) Patent No.: US 11,105,823 B2
(45) Date of Patent: Aug. 31, 2021

(54) METHODS AND COMPOSITIONS FOR IDENTIFYING NON-ALCOHOLIC FATTY LIVER DISEASE

(71) Applicant: The Regents of the University of California, Oakland, CA (US)

(72) Inventors: Edward A. Dennis, La Jolla, CA (US); Oswald Quehenberger, San Diego, CA (US); Rohit Loomba, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 149 days.

(21) Appl. No.: 15/550,706

(22) PCT Filed: Feb. 12, 2016

(86) PCT No.: PCT/US2016/017822
§ 371 (c)(1),
(2) Date: Aug. 11, 2017

(87) PCT Pub. No.: WO2016/130961
PCT Pub. Date: Aug. 18, 2016

(65) Prior Publication Data
US 2018/0031585 A1    Feb. 1, 2018

Related U.S. Application Data

(60) Provisional application No. 62/116,108, filed on Feb. 13, 2015.

(51) Int. Cl.
*G01N 33/92*    (2006.01)
*G01N 33/88*    (2006.01)
*G01N 33/68*    (2006.01)

(52) U.S. Cl.
CPC ......... *G01N 33/92* (2013.01); *G01N 33/6893* (2013.01); *G01N 33/88* (2013.01);
(Continued)

(58) Field of Classification Search
CPC ..... G01N 33/92; G01N 33/6893; G01N 33/88
See application file for complete search history.

(56) References Cited

U.S. PATENT DOCUMENTS 10,422,786 B2 *    9/2019  Loomba .............. G01N 30/7233
2010/0233724 A1    9/2010  Watkins et al.
(Continued)

FOREIGN PATENT DOCUMENTS

| WO | 2011/140093 A2 | 11/2011 |
| WO | 2012000770 A1 | 1/2012 |
| WO | 2015/089102 A1 | 6/2015 |

OTHER PUBLICATIONS

Polyunsaturated fatty acid metabolites as novel lipidomic biomarkers for noninvasive diagnosis of nonalcoholic steatohepatitis Rohit Loomba, Oswald Quehenberger, Aaron Armando, Edward A. Dennis Journal of Lipid Reasearch vol. 56, 2015 (Year: 2015).*

(Continued)

*Primary Examiner* — Brian R Gordon
*Assistant Examiner* — Dwan A Gerido
(74) *Attorney, Agent, or Firm* — Gavrilovich, Dodd & Lindsey LLP

(57) ABSTRACT

The disclosure provides methods for differentiating between non-alcoholic fatty liver disease and non-alcoholic steatohepatitis. The method includes measuring eicosanoids and fatty acid levels in a biological sample.

7 Claims, 12 Drawing Sheets

(52) U.S. Cl.
CPC ..... *G01N 2405/00* (2013.01); *G01N 2570/00* (2013.01); *G01N 2800/085* (2013.01); *G01N 2800/7085* (2013.01)

(56) References Cited

U.S. PATENT DOCUMENTS

| | | | | |
|---|---|---|---|---|
| 2013/0056630 A1* | 3/2013 | Feldstein | ........... | G01N 33/6893 |
| | | | | 250/282 |
| 2013/0126722 A1* | 5/2013 | Kamp | ................ | G01N 33/6812 |
| | | | | 250/282 |
| 2020/0011848 A1* | 1/2020 | Loomba | ................ | G16B 20/00 |

OTHER PUBLICATIONS

Wittmann-Regis, Agnes, International Preliminary Report on Patentability and Written Opinion, PCT/US2016/07822, The International Bureau of WIPO, dated Aug. 24, 2017.

Copenheaver, Blain R., Written Opinion on the International Searching Authority, PCT/US2016/07822, United States Patent & Trademark Office, dated May 26, 2016.

Loomba et al., "Polyunsaturated fatty acid metabolites as novel lipidomic biomarkers for noninvasive diagnosis of nonalcoolic steatohepatitis," J. Lipid Res., 56(1):185-192, epub Nov. 17, 2014.

Puri, Puneet et al., "The plasma lipidomic signature of nonalcoholic steatohepatitis", Hepatology, vol. 50, No. 6, Aug. 10, 2009, pp. 1827-1838.

Stricker, J., Extended European Search Report, Application No. 16749993.8, European Patent Office, dated Jun. 1, 2018.

* cited by examiner

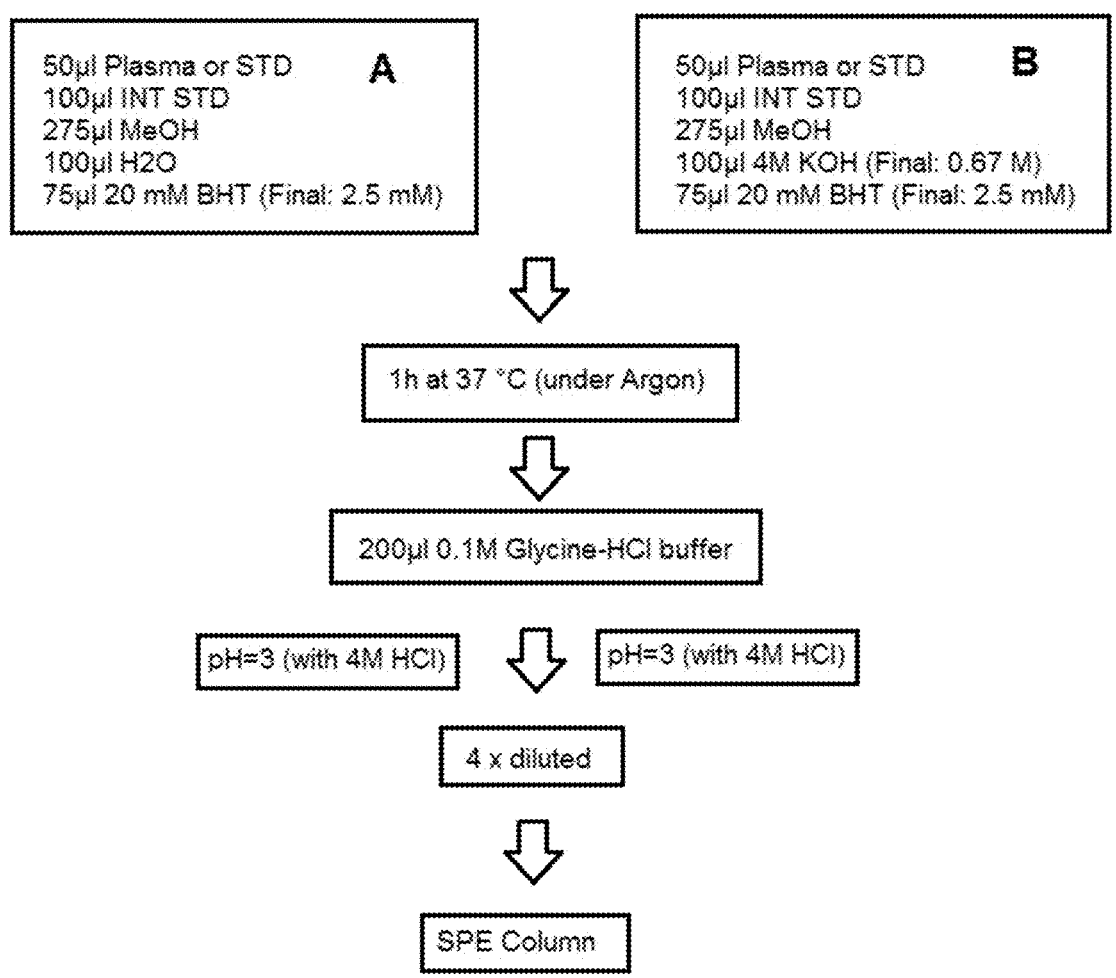
FIG. 1A-B

METHODS AND COMPOSITIONS FOR IDENTIFYING NON-ALCOHOLIC FATTY LIVER DISEASE

CROSS REFERENCE TO RELATED APPLICATIONS

This application is a U.S. National Stage Application filed under 35 U.S.C. § 371 and claims priority to International Application No. PCT/US2016/017822, filed Feb. 12, 2016, which application claims priority under 35 U.S.C. § 119(e) of U.S. Provisional Appl. No. 62/116,108, filed Feb. 13, 2015, which are incorporated herein by reference.

STATEMENT REGARDING FEDERALLY SPONSORED RESEARCH

This invention was made with government support under DK090303 and GM069338 awarded by the National Institutes of Health. The government has certain rights in the invention.

FIELD OF THE INVENTION

The invention relates in general to materials and methods to determine fatty liver disease and non-alcoholic steatohepatitis.

BACKGROUND

Fatty liver disease (or steatohepatis) is often associated with excessive alcohol intake or obesity, but also has other causes such as metabolic deficiencies including insulin resistance and diabetes. Fatty liver results from triglyceride fat accumulation in vacuoles of the liver cells resulting in decreased liver function, and possibly leading to cirrhosis or hepatic cancer.

Non-alcoholic fatty liver disease (NAFLD) represents a spectrum of disease occurring in the absence of alcohol abuse.

SUMMARY

The disclosure provides a method of differentiating non-alcoholic steatohepatitis (NASH) from nonalcoholic fatty liver (NAFL) in a subject. The method includes obtaining a biological sample from the subject; treating the sample with an alkaline solution to release esterified eicosanoids and recovering the eicosanoids; and comparing the levels of at least one esterified eicosanoid in the biological sample obtained from the subject to a control sample obtained from a NAFL subject, wherein a difference in the levels of the at least one eicosanoid in the sample obtained from the subject compared to the control is indicative of NASH. In one embodiment, the eicosanoids measured are eicosanoids recovered at greater than 60%. In another embodiment of any of the foregoing embodiments, the eicosanoids are selected from the group consisting of 8-HETrE and 15-HETrE. In another embodiment of any of the foregoing the biological sample is selected from the group consisting of blood, blood plasma and blood serum. In yet another embodiment of any of the foregoing the method further comprises adding butylated hydroxytoluene (BHT) prior to alkaline treatment. In a further embodiment, BHT is about 2.5 mM. In another embodiment of any of the foregoing, the alkaline solution is aqueous potassium hydroxide (KOH). In a further embodiment, KOH is used at about 0.6-0.7M KOH. In another embodiment of any of the foregoing embodiments, an increase in the levels of the at least one eicosanoid in the sample obtained from the subject compared to the control is indicative of NASH. In yet another embodiment, the method further comprises measuring the level of omega-3 fatty acid DHA and/or 17-HDoHE in the sample, wherein an increase compared to control is indicative of NASH. In any of the foregoing embodiments, the eicosanoids are measured by liquid chromatography. In any of the foregoing embodiments, fatty acids are measured by gas chromatography mass spectrometry.

The disclosure also provides a method of differentiating nonalcoholic steatohepatitis (NASH) from nonalcoholic fatty liver (NAFL) in a subject, comprising obtaining a biological sample from the subject; treating the sample with an alkaline solution; and recovering eicosanoids and fatty acids from the treated sample; and comparing the levels of at least one biomarker in the biological sample obtained from the subject to a control sample with known NAFL, wherein an increase in the levels of the at least one biomarker in the sample obtained from the subject compared to the control is indicative of NASH, and further wherein the biomarkers are selected from the group consisting of 8-HETrE, 15-HETrE, DHA, 17-HDoHE and any combination thereof. In one embodiment, the eicosanoids measured are eicosanoids recovered at greater than 60%. In another embodiment, the at least one biomarker comprises 8-HETrE or 15-HETrE. In yet another embodiment, the biological sample is selected from the group consisting of blood, blood plasma and blood serum. In still another embodiment of any of the foregoing, the method further comprises adding butylated hydroxytoluene (BHT) prior to alkaline treatment. In a one embodiment, the alkaline treatment comprises adding aqueous potassium hydroxide (KOH). In a further embodiment, the KOH is added to about 0.6 to 0.7M KOH. In still another embodiment, about 2.5 mM BHT is used. In yet another embodiment of any of the foregoing, the method further comprises measuring the level of omega-3 fatty acid DHA and/or 17-HDoHE in the sample, wherein an increase compared to control is indicative of NASH. In another embodiment, the eicosanoids are measured by liquid chromatography and the fatty acids are measured by gas chromatography mass spectrometry. In still a further embodiment of any of the foregoing, the level of proinflammatory eicosanoids selected from the group consisting of 5-HETE, 8-HETE, 11-HETE, 15-HETE, 13-HODE, 9-oxoODE and any combination thereof are measuredwherein levels of any of the foregoing that are lower than a NAFL control is indicative of NASH.

BRIEF DESCRIPTION OF THE DRAWINGS

FIG. 1A-B shows a scheme for eicosanoid determination. (A) Control without alkaline hydrolysis and (B) total eicosanoids with alkaline hydrolysis.

DETAILED DESCRIPTION

Figure 2A:
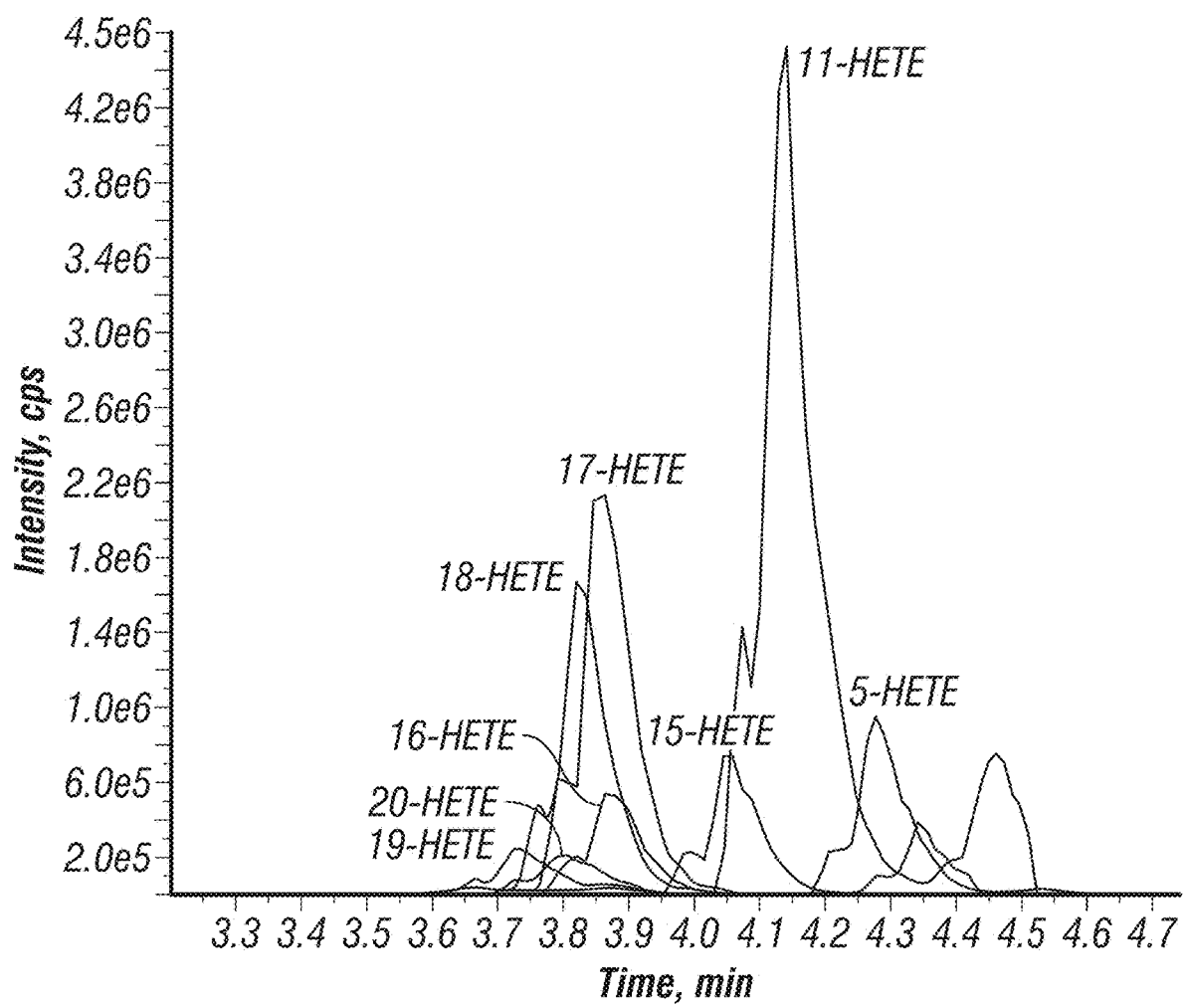
FIG. 2A-B shows an extracted chromatograph for a selection of HETEs before (A) and after (B) exposure to alkaline hydrolysis conditions.

As used herein and in the appended claims, the singular forms "a," "and," and "the" include plural referents unless the context clearly dictates otherwise. Thus, for example, reference to "a derivative" includes a plurality of such derivatives and reference to "a subject" includes reference to one or more subjects and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Non-alcoholic fatty liver disease (NAFL or NAFLD) represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). NAFLD is linked to insulin resistance, it causes liver disease in adults and children and may ultimately lead to cirrhosis (Skelly et al., J Hepatol., 35: 195-9, 2001; Chitturi et al., Hepatology, 35(2):373-9, 2002). The severity of NAFLD ranges from the relatively benign isolated predominantly macrovesicular steatosis (i.e., non-alcoholic fatty liver or NAFL) to non-alcoholic steatohepatitis (NASH) (Angulo et al., J Gastroenterol Hepatol, 17 Suppl:S186-90, 2002). NASH is characterized by the histologic presence of steatosis, cytological ballooning, scattered inflammation and pericellular fibrosis (Contos et al., Adv Anat Pathol., 9:37-51, 2002). Hepatic fibrosis resulting from NASH may progress to cirrhosis of the liver or liver failure, and in some instances may lead to hepatocellular carcinoma.

The degree of insulin resistance (and hyperinsulinemia) correlates with the severity of NAFLD, being more pronounced in patients with NASH than with simple fatty liver (Sanyal et al., Gastroenterology, 120(5):1183-92, 2001). As a result, insulin-mediated suppression of lipolysis occurs and levels of circulating fatty acids increase. Two factors associated with NASH include insulin resistance and increased delivery of free fatty acids to the liver. Insulin blocks mitochondrial fatty acid oxidation. The increased generation of free fatty acids for hepatic re-esterification and oxidation results in accumulation of intrahepatic fat and increases the liver's vulnerability to secondary insults.

The prevalence of NAFLD in children is unknown because of the requirement of histologic analysis of liver in order to confirm the diagnosis (Schwimmer et al., Pediatrics, 118(4):1388-93, 2006). However, estimates of prevalence can be inferred from pediatric obesity data using hepatic ultra-sonongraphy and elevated serum transaminase levels and the knowledge that 85% of children with NAFLD are obese. Data from the National Health and Nutrition Examination Survey has revealed a threefold rise in the prevalence of childhood and adolescent obesity over the past 35 years; data from 2000 suggests that 14-16% children between 6-19 yrs age are obese with a BMI>95% (Fishbein et al., J Pediatr. Gastroenterol. Nutr., 36(1):54-61, 2003), and also that fact that 85% of children with NAFLD are obese.

In patients with histologically proven NAFLD, serum hepatic aminotransferases, specifically alanine aminotransferase (ALT), levels are elevated from the upper limit of normal to 10 times this level (Schwimmer et al., J Pediatr., 143(4):500-5, 2003; Rashid et al., J Pediatr Gastroenterol Nutr., 30(1):48-53, 2000). The ratio of ALT/AST (aspartate aminotransferase) is >1 (range 1.5-1.7) which differs from alcoholic steatohepatitis where the ratio is generally <1. Other abnormal serologic tests that may be abnormally elevated in NASH include gamma-glutamyltransferase (gamma-GT) and fasting levels of plasma insulin, cholesterol and triglyceride.

The exact mechanism by which NAFLD develops into NASH remains unclear. Because insulin resistance is associated with both NAFLD and NASH, it is postulated that other additional factors are also required for NASH to arise. This is referred to as the "two-hit" hypothesis (Day C P. Best Pract. Res. Clin. Gastroenterol., 16(5):663-78, 2002) and involves, firstly, an accumulation of fat within the liver and, secondly, the presence of large amounts of free radicals with increased oxidative stress. Macrovesicular steatosis represents hepatic accumulation of triglycerides, and this in turn is due to an imbalance between the delivery and utilization of free fatty acids to the liver. During periods of increased calorie intake, triglyceride will accumulate and act as a reserve energy source. When dietary calories are insufficient, stored triglycerides (in adipose) undergo lipolysis and fatty acids are released into the circulation and are taken up by the liver. Oxidation of fatty acids will yield energy for utilization.

The eicosanoid biosynthetic pathway includes over 100 bioactive lipids and relevant enzymes organized into a complex and intertwined lipid-signaling network. Biosynthesis of polyunsaturated fatty acid (PUFA) derived lipid mediators is initiated via the hydrolysis of phospholipids by phospholipase $A_2$ (PLA$_2$) upon physiological stimuli. These PUFA including arachidonic acid (AA), dihomo-gamma-linolenic acid (DGLA), eicosapentaenoic acid (EPA), and docosahexaenoic acid (DHA) are then processed by three enzyme systems: lipoxygenases (LOX), cyclooxygenases (COX) and cytochrome P450s, producing three distinct lineages of oxidized lipid classes. These enzymes are all capable of converting free arachidonic acid and related PUFA to their specific metabolites and exhibit diverse potencies, half-lives and utilities in regulating inflammation and signaling. Additionally, non-enzymatic processes can result in oxidized PUFA metabolites including metabolites from the essential fatty acids linoleic (LA) and alpha-linolenic acid (ALA).

Eicosanoids, which are key regulatory molecules in metabolic syndromes and the progression of hepatic steatosis to steatohepatitis in nonalcoholic fatty liver disease (NAFLD), act either as anti-inflammatory agents or as pro-inflammatory agents. Convincing evidence for a causal role of lipid peroxidation in steatohepatitis has not been unequivocally established; however, a decade of research has strongly suggested that these processes occur and that oxidative-stress is associated with hepatic toxicity and injury. As discussed above, nonalcoholic fatty liver disease (NAFLD) encompasses a wide spectrum of histological cases associated with hepatic fat over-accumulation that range from nonalcoholic fatty liver (NAFL) to nonalcoholic steatohepatitis (NASH). It is distinguished from NAFL by evidence of cytological ballooning, inflammation, and higher degrees of scarring and fibrosis. Hence, NASH is a serious condition, and approximately 10-25% of inflicted patients eventually develop advanced liver disease, cirrhosis, and hepatocellular carcinoma.

Thus, it is important to differentiate NASH from NAFL. At the present time, the gold standard technique for the diagnosis of NASH is a liver biopsy examination, which is recognized as the only reliable method to evaluate the presence and extent of necro-inflammatory changes, presence of ballooning and fibrosis in liver. However, liver biopsy is an invasive procedure with possible serious complications and limitations. Reliable noninvasive methods are therefore needed to avoid the sampling risks. It is proposed that differences in plasma levels of free eicosanoids can distinguish NAFL from NASH based on studies of well-characterized patients with biopsy substantiated NAFL and NASH.

Alterations in lipid metabolism may give rise to hepatic steatosis due to increased lipogenesis, defective peroxisomal and mitochondrial β-oxidation, and/or a lower ability of the liver to export lipids resulting in changes in fatty acids and/or eicosanoids. Some studies have highlighted the role of triacylglycerol, membrane fatty acid composition, and very low density lipoprotein (VLDL) production in the development of NASH and associated metabolic syndromes.

Cyclooxygenase-2 (COX-2), a key enzyme in eicosanoid metabolism, is abundantly expressed in NASH, which promotes hepatocellular apoptosis in rats. Others have reported that oxidized lipid products of LA including 9-hydroxyoctadienoic acid (9-HODE), 13-HODE, 9-oxooctadienoic acid (9-oxoODE), and 13-oxoODE as well as of arachidonic acid 5-hydroxyeicosa-tetraenoic acid (5-HETE), 8-HETE, 11-HETE, and 15-HETE are linked to histological severity in nonalcoholic fatty liver disease.

Free fatty acids are cytotoxic; thus the majority of all fatty acids in mammalian systems are esterified to phospholipids and glycerolipids as well as other complex lipids. Similarly, oxygenated metabolites of fatty acids can exist either in their free form or esterified to complex lipids. To capture all esterified eicosanoids for analysis, a saponification step is used to release them. However, the stability of eicosanoids under these conditions has not been studied in detail and the process has been suspected to lead to degradation and poor quantification. Using a library of 173 standards, experiments were performed to assess the stability and recover of each metabolite after exposure to alkaline hydrolysis conditions.

The disclosure provides methods, kits and compositions useful for differentiation NAFL from NASH. Such methods will help in the early onset and treatment of disease. Moreover, the methods reduce biopsy risks associated with liver biopsies currently used in diagnosis. The methods and compositions comprise modified eicosanoids and PUFAs in the diagnosis. As such, the biomarkers are manipulated from their natural state by chemical modifications to provide a derived biomarker that is measured and quantitated. The amount of a specific biomarker can be compared to normal standard sample levels (i.e., those lacking any liver disease) or can be compared to levels obtained from a diseased population (e.g., populations with clinically diagnosed NASH or NAFL).

Levels of free eicosanoids and PUFA metabolites can be expressed as AUROC (Area under Receiver Operating Characteristic Curve). AUROC is determined by measuring levels of free eicosanoids and PUFA metabolites by stable isotope dilution. Briefly, identical amounts of deuterated internal standards are added to each sample and to all the primary standards used to generate standard curves. Levels of eicosanoids and PUFA metabolites are calculated by determining the ratios between endogenous metabolite and matching deuterated internal standards. Ratios are converted to absolute amounts by linear regression. Individual eicosanoid metabolites are assessed for diagnostic test performances and capability to differentiating between NAFL and NASH using statistical analyses including chi-square test, t-test and AUROC.

The method of the disclosure comprises determining the level of one or more free eicosanoids and/or polyunsaturated fatty acid (PUFA) metabolites in a sample of a patient. As used herein, the term "sample" refers to any biological sample from a patient. Examples include, but are not limited to, saliva, hair, skin, tissue, sputum, blood, plasma, serum, vitreal, cerebrospinal fluid, urine, sperm and cells. In one embodiment, the sample is a plasma sample.

Lipids are extracted from the sample, as detailed further in the Examples. The identity and quantity of eicosanoids and/or PUFA metabolites in the extracted lipids is first determined and then compared to suitable controls. The determination may be made by any suitable lipid assay technique, such as a high throughput including, but not limited to, spectrophotometric analysis (e.g., colorimetric sulfo-phospho-vanillin (SPV) assessment method of Cheng et al., Lipids, 46(1):95-103 (2011)). Other analytical methods suitable for detection and quantification of lipid content will be known to those in the art including, without limitation, ELISA, NMR, UV-Vis or gas-liquid chromatography, HPLC, UPLC and/or MS or RIA methods enzymatic based chromogenic methods. Lipid extraction may also be performed by various methods known to the art, including the conventional method for liquid samples described in Bligh and Dyer, Can. J. Biochem. Physiol., 37, 91 1 (1959).

For discrimination of NAFL from NASH, the values obtained are compared to normal controls, subjects with NAFL and/or subjects with NASH. The disclosure demonstrates that 8-HETrE and 15-HETrE are increased in NASH subjects compared to NAFL subjects. Moreover, these values can be used in combination with measurements of the omega-3 fatty acid DHA ($p<0.001$) and/or its metabolite 17-HDoHE. Accordingly, the disclosure can use one or a combination of any of the markers selected from the group consisting of 8-HETrE, 15-HETrE, omega-3 fatty acid DHA and 17-HDoHE in the methods of the disclosure. These marker(s) can be used in combination with existing diagnostics as described herein in determining NAFL or NASH. An increase in markers selected from the group consisting of 8-HETrE, 15-HETrE, omega-3 fatty acid DHA, 17-HDoHE and any combination thereof compared to a control and/or NAFL subject is indicative of NASH.

Thus, an increase in markers selected from the group consisting of 8-HETrE, 15-HETrE, omega-3 fatty acid DHA and 17-HDoHE is indicative of an increased risk of progression of the liver disease and/or the desired differentiation of NASH, for which therapy can be applied accordingly.

Levels of free eicosanoids and PUFA metabolites can be expressed as AUROC (Area under Receiver Operating Characteristic Curve). AUROC is determined by measuring levels of free eicosanoids and PUFA metabolites by stable isotope dilution. Briefly, identical amounts of deuterated internal standards are added to each sample and to all the primary standards used to generate standard curves. Levels of eicosanoids and PUFA metabolites are calculated by determining the ratios between endogenous metabolite and matching deuterated internal standards. Ratios are converted to absolute amounts by linear regression. Individual eicosanoid metabolites are assessed for diagnostic test performances and capability to differentiating between NAFL and NASH using statistical analyses including chi-square test, t-test and AUROC.

An increased of AUROC values of about at least 0.8, about at least 0.9, about at least 0.95, about at least 0.96, about at least 0.97, about at least 0.98, about at least 0.99 or 1.0 are indicative of a difference sufficient in determining NASH.

The methods of the disclosure utilize a process that optimizes the amount of eicosanoids and PUFA that can be obtained. The disclosure, thus, provides methods and compositions that preserve and minimize degradation of lipid metabolites during alkaline treatment, and to identify specific eicosanoids and related oxidized PUFA released from esterified lipids that can serve as biomarkers for disease.

It is to be understood that while the disclosure has been described in conjunction with specific embodiments thereof, that the foregoing description as well as the examples which follow are intended to illustrate and not limit the scope of the disclosure. Other aspects, advantages and modifications within the scope of the disclosure will be apparent to those skilled in the art to which the disclosure.

EXAMPLES

Reagents. All reagents are HPLC grade and were purchased from Fisher Scientific.

Lipid hydrolysis and extraction. To extract total eicosanoids, 50 µl plasma, spiked with 100 µl of a cocktail of 25 deuterated internal standards in methanol (individually purchased from Cayman Chemicals, Ann Arbor, Mich.), were subjected to alkaline treatment (0.66 M KOH) for 1 hour at 37° C. to hydrolyze esterified fatty acids. To prevent lipid autoxidation, 2.5 mM butylated hydroxytoluene (BHT) was added to the mixture prior to KOH treatment. This optimal antioxidant concentration was chosen based on preliminary tests with varying concentrations of BHT ranging from none to 10 mM, demonstrating ineffectiveness at less than 1 mM, but crystallization at 5 mM. Distilled water was added instead of KOH in the control (FIG. 1).

The plasma samples containing internal standards and KOH were incubated in tubes under an argon atmosphere at 37° C. for 1 h to release the free fatty acids. Lipid degradation was determined with purified standards treated with or without KOH and the results were expressed as percent recovery. At the end of hydrolysis, 200 µl of 0.1 M glycine-HCl buffer (pH 3.0) was added and the final pH was adjusted to pH=3 with the slow addition of 4 M HCl. In order to minimize salt interference during the isolation of eicosanoids by solid phase extraction, each sample was diluted to a final volume of 3 ml with $H_2O$.

Lipid metabolites were isolated by solid phase extraction on a Strata-X polymeric reversed phase column (Phenomenex, Torrance, Calif.), using an activation procedure of consecutive washes with 3.5 ml of 100% methanol followed by 3.5 ml of water. The samples were loaded and eicosanoids were then eluted with 1 ml of 100% methanol. The eluent was dried under vacuum and dissolved in 100 µl of buffer A, consisting of 60/40/0.02 (v/v/v) water/acetonitrile/acetic acid and immediately used for analysis.

Standard curve and internal standard. Preliminary trials indicated significant degradation of certain eicosanoid metabolites in the process of saponification; therefore, a cocktail of 25 deuterated internal standards was subjected to the same alkaline conditions, followed by acidification and isolation. Thirteen point standard curves were generated for 148 primary standards ranging from 0.005 to 5.0 ng, and containing 1 ng of each of the internal standards added as a mixture consisting of 25 deuterated eicosanoids. The methodology contains 173 MRM pairs (148 metabolites+25 deuterated internal standards) for eicosanoids and related metabolites, which are monitored in a single 5 min LC/MS/MS analysis (Dumlao et al., Biochim, Biophys. Acta, 1811: 724-736, 2011; Quehenberger et al., BBA—Mol. Cell Biol. Lipids, 1811:648-656, 2011).

Separation and quantification of Eicosanoids. Separation was performed on an Acquity ultra-performance liquid chromatography (UPLC) system (Waters, Milford, Mass., USA), equipped with RP18 column (2.1×100 mm; 1.7 µm; Waters). The mobile phase condition and mass spectrometer parameters are described in Wang et al. (J. Chromatogr., 1359:60-69, 2014). Data was collected on an AB/Sciex 6500 QTRAP hybrid, triple quadrupole mass spectrometry using negative electrospray and scheduled multiple reaction monitoring (MRM) mode.

Recovery rates were determined by comparing peak areas using a set of 173 purified standards containing all internal standards before and after treatment with KOH. All determinations were performed in triplicate and the average value reported. The precision of the quantitation was determined by the coefficient of variation (CV), calculated from the mean of three replicates and expressed as the relative standard deviation (% RSD).

Total fatty acid determination. Plasma samples were spiked with deuterated internal standards and then derivatized and the individual free fatty acids were quantified by Gas Chromatography Mass Spectrometry (GC-MS) by the method of Quehenberger et al. (supra). Total fatty acids value from GC-MS were obtained, no degradation was observed during alkaline hydrolysis.

Plasma preparation. Plasma samples were collected from patients and healthy volunteers; the detailed description of the patients in the study population including baseline demographic, clinical, biochemical and histologic characteristics is provided in Loomba et al. (J. Lipid Res., 56:185-192, 2014) and is summarized in Table 1. Patients with NAFLD were diagnosed and confirmed by liver biopsy examination; patients with other causes of liver disease were excluded. All patients underwent a standard history and physical exam, biochemical testing, and the magnetic resonance imaging-estimated proton density fat fraction (MRI-PDFF). On the basis of the liver histology, subjects with NAFLD were divided into two groups, those with NAFL and those with NASH. Collected plasma samples were stored at −80° C. The total amount of each eicosanoid was determined from immediately thawed samples.

TABLE 1

Baseline demographic and histological characteristics of the patients in the study population.

|  | Controls n = 3 | NAFL n = 10 | NASH n = 9 | NAFL vs. NASH P-values |
|---|---|---|---|---|
| Age | 45.03 ± 23.02 | 48.90 ± 14.03 | 45.89 ± 12.94 | 0.633 |
| Sex | 33% male | 40% male | 44% male |  |
| BMI | 22.42 ± 6.59 | 29.49 ± 5.39 | 29.59 ± 5.01 | 0.966 |
| Liver Histology |  |  |  |  |
| Steatosis |  | 0.75 ± 0.5 | 2.33 ± 0.82 | 0.005 |
| Fibrosis |  | 0 ± 0 | 1.60 ± 0.89 | 0.016 |
| NAS |  | 1.75 ± 0.5 | 6.33 ± 1.03 | 0.0001 |
| Hep. Balloon. |  | 0 ± 0 | 1.50 ± 0.84 | 0.007 |
| Lob. Infl. |  | 1 ± 0 | 2.17 ± 0.41 | 0.001 |
| Portal Infl. |  | 0.5 ± 0.55 | 0.17 ± 0.41 | 0.262 |

Destruction of Oxidized PUFA by Alkaline Treatment. The stability of eicosanoids after exposure to strong alkaline conditions was analyzed using a set of deuterated internal standards (Table 2). It is conceivable that strong base catalyzes the exchange of deuterium with hydrogen in addition to destruction of the molecule. As all mass spectral data need to be normalized to internal standards, it is important to differentiate between these two independent events. Previously established MRM transitions that were employed for the analysis of free eicosanoids were used (Wang et al. supra). The recovery rate of the specific deuterated internal standards subjected to conditions that are used for alkaline hydrolysis of esters is summarized in Table 1. The pretreatment with the alkaline hydrolysis solution completely destroyed all deuterated prostaglandins and their derivatives as well as the leukotrienes. The other deuterated internal standards were also degraded to various extents. Only arachidonic acid and its hydroxylated metabolite 20-HETE showed full recovery (Table 2) and they showed similar recovery rates compared with their corresponding non-deuterated primary standards also measured by UPLC/MS. The result indicated deuterium was not exchanged under hydrogen at alkaline conditions.

TABLE 2

Recovery of deuterated internal standards subjected to alkaline hydrolysis.

| Internal standard | Control (Intensity × $10^4$) | RSD (%) | Saponified (Intensity × $10^4$) | RSD (%) | Recovery (%) |
|---|---|---|---|---|---|
| (d8) AA | 25.3 | 17 | 23.1 | 7.9 | 91 |
| (d4) 9,10 diHOME | 44.8 | 11 | 23.0 | 1.8 | 51 |
| (d4) 12,13 diHOME | 47.5 | 12 | 27.7 | 1.3 | 58 |
| (d11) 8,9 EET | 8.2 | 15 | 3.5 | 11 | 43 |
| (d11) 11,12 EET | 8.7 | 11 | 3.1 | 7.7 | 35 |
| (d11) 14,15 EET | 13.1 | 12 | 3.3 | 9.6 | 25 |
| (d8) 5-HETE | 23.9 | 10 | 11.8 | 1 | 49 |
| (d8) 12-HETE | 14.4 | 9.1 | 10.9 | 1.1 | 76 |
| (d8) 15-HETE | 36.7 | 6.8 | 21.8 | 11 | 59 |
| (d6) 20-HETE | 15.6 | 14.0 | 17.4 | 8.9 | 110 |
| (d4) 9-HODE | 60.0 | 8.7 | 23.9 | 12 | 40 |
| (d4) 13-HODE | 67.3 | 9.1 | 28.4 | 9.6 | 42 |
| (d4) LTB4 | 27.1 | 19 | 4.0 | 12 | 15 |
| (d5) LTC4 | 0.04 | 13 | ND | 0 | 0 |
| (d5) LTE4 | 7.9 | 7.8 | 0.80 | 35 | 9.6 |
| (d4) PGD2 | 22.8 | 12 | ND | 0 | 0 |
| (d4) dhk PGD2 | 18.9 | 7.8 | ND | 0 | 0 |
| (d4) PGE2 | 6.4 | 16 | ND | 0 | 0 |
| (d4) 6 k PGF1a | 9.1 | 9.1 | 1.2 | 6.2 | 13 |
| (d4) PGF2a | 5.8 | 11 | 2.9 | 5 | 49 |
| (d4) dhk PGF2a | 7.8 | 1.1 | 2.3 | 6.7 | 29 |
| (d11) 8-iso PGF2a III | 0.90 | 5.0 | ND | 0 | 0 |
| (d4) 15d PGJ2 | 566 | 1.3 | ND | 0 | 0 |
| (d4) TXB2 | 21.1 | 11 | 6.1 | 5 | 29 |
| (d4) Resolvin E1 | 5.7 | 0.3 | 1.5 | 12 | 26 |

Figure 2B:
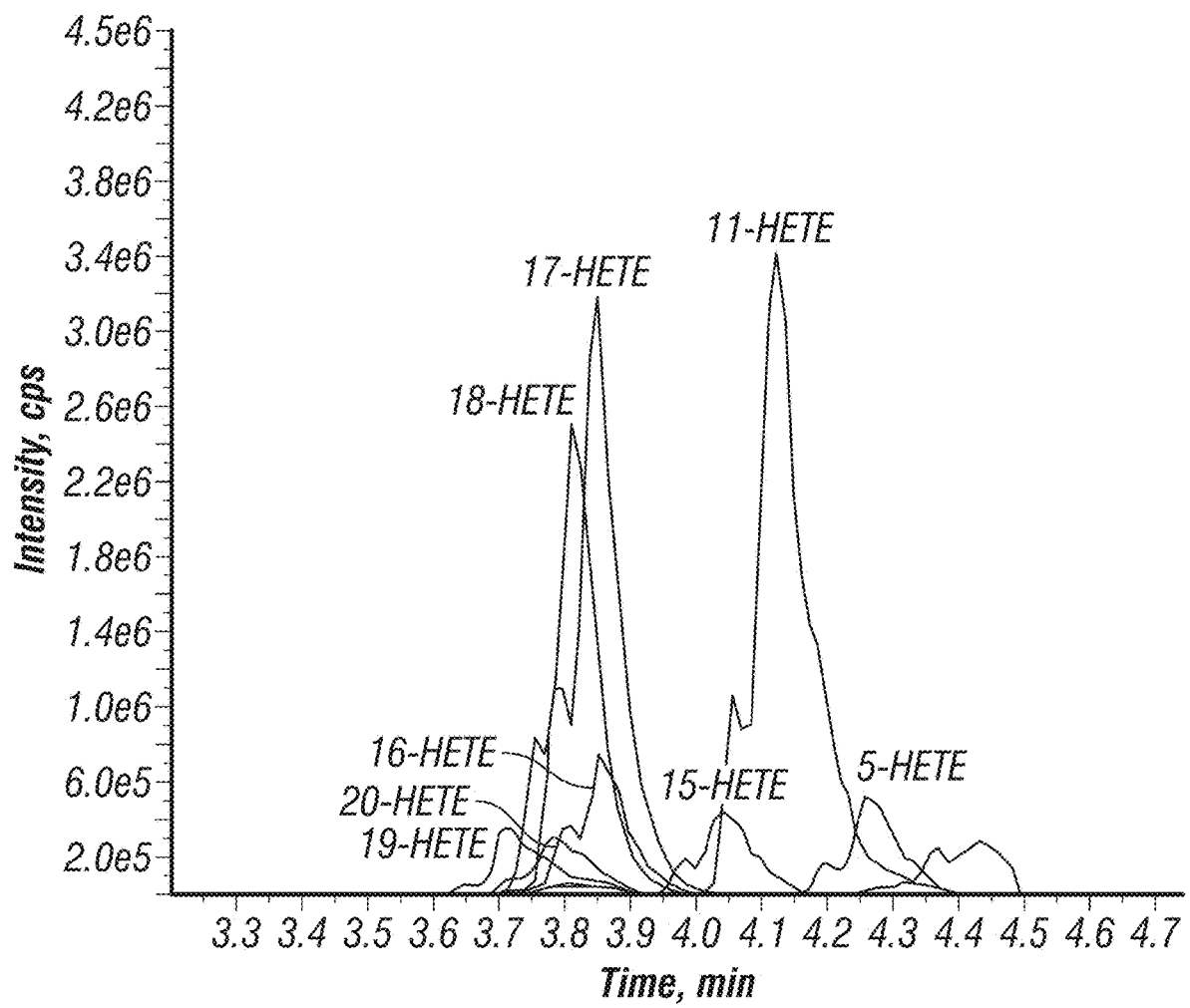

To determine whether the poor recovery for some of the internal standards was due to loss of the deuterium label or destruction of the molecular structure, we expanded our stability tests and examined all 148 primary eicosanoid standards that we typically use for profiling for their resistance to base-induced degradation. As shown in FIG. 2 and Table 3, many of the eicosanoids are susceptible to base induced degradation, as exemplified by their changes in mass spectral intensities. In particular, all prostaglandins and leukotrienes were completely destroyed. Similarly, a number of eicosanoids containing epoxy or keto groups underwent degradation to various degrees. Interestingly, the signal intensities of some metabolites including 16-HETE, 17-HETE, 18-HETE, 19-HETE, 20-HETE increased after exposure to saponifying conditions when compared with their original peaks prior to exposure to strong alkali (FIG. 2). This may be the result of base-induced metabolite conversion and autoxidation.

The precision of the analysis (RSD, %) was determined in three independent analytical runs of all 173 standards (148 metabolites and 25 deuterated internal standards) with or without saponification and demonstrated that the assay was highly reproducible. In general, the RSD was less than 10% for most of the metabolites (Table 3).

For application in the analysis of esterified eicosanoids in biological samples including human plasma, a panel of eicosanoids was compiled that were either resistant to base-induced degradation or suffered only minor but reproducible destruction. For practical purpose a cut-off point of 60% and a RSD of less than 10% was used to assemble a list of eicosanoids that satisfied these criteria (Table 2).

NAFL vs NASH Oxidized PUFA in Plasma. This protocol was then applied to the analysis of human plasma. Previous studies have looked at lipid extraction. Those studies used alkaline-hydrolysis to liberate the fatty acids before analysis, but did not report testing the effect of strong bases on eicosanoid stability. Considering the limitations outlined in Table 3 and using the algorithm for the identification of stable metabolites summarized in Table 2, a number of eicosanoids were identified and quantified that were present in the plasma of control, NAFL and NASH patients and are shown in FIG. 3 to FIG. 7. Differences between the NAFL and NASH groups were assessed with a Student's t-test. Statistically significant differences for NAFL/NASH with $p<0.05$ were observed and shown in FIGS. 5 and 7.

Figure 3:
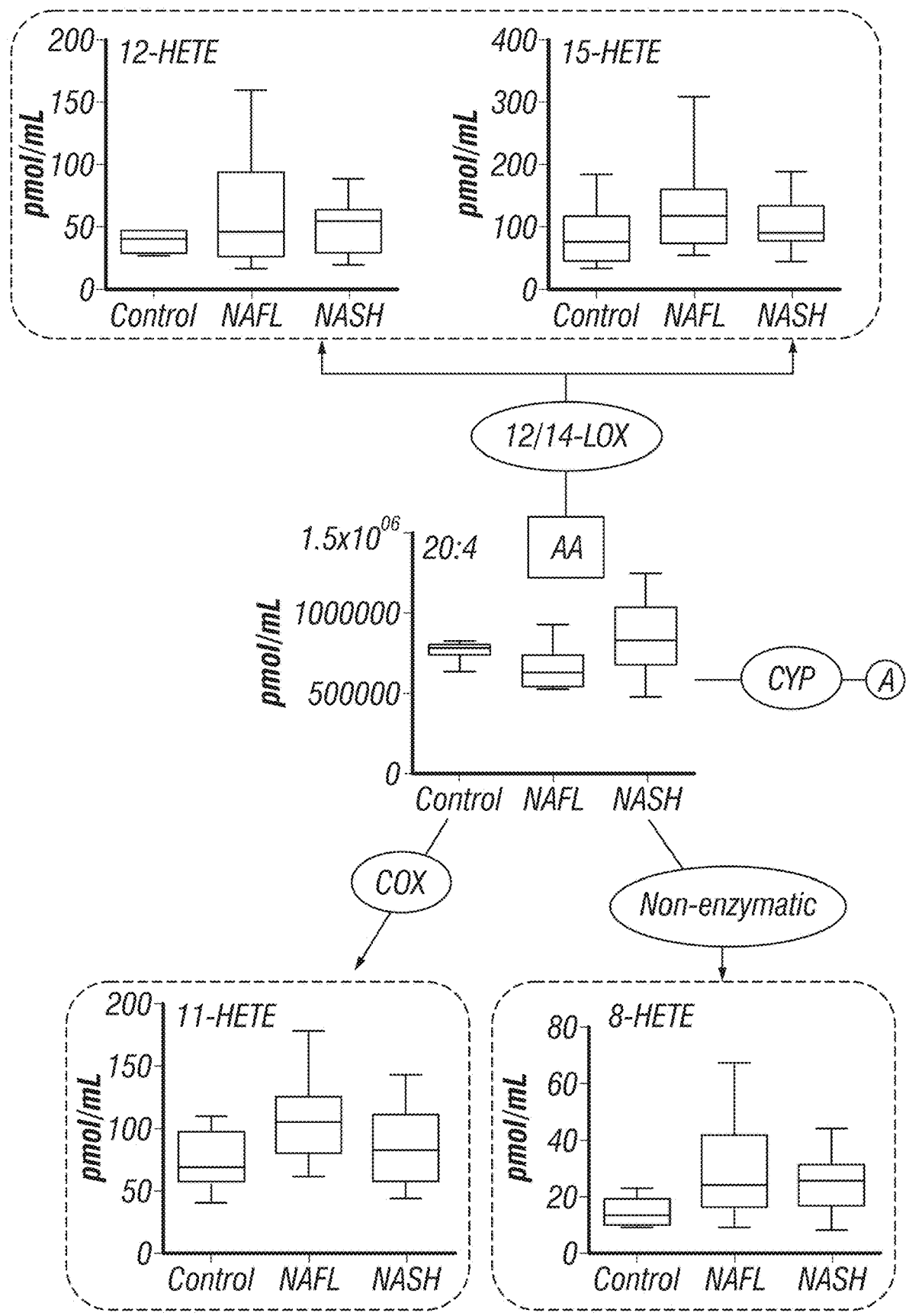
FIG. 3 shows arachidonic acid (AA) derived metabolites. The amounts of total AA and its metabolites derived from COX, LOX, CYP, and non-enzymatic pathways in plasma are shown in the three clinical arms for each metabolite. The lower end of the whisker box indicates the 25th percentile, the line in the box indicates the 50th percentile, and the upper end indicates the 75th percentile. The whiskers indicate the low and upper extremes of the measurements.
Figure 3:
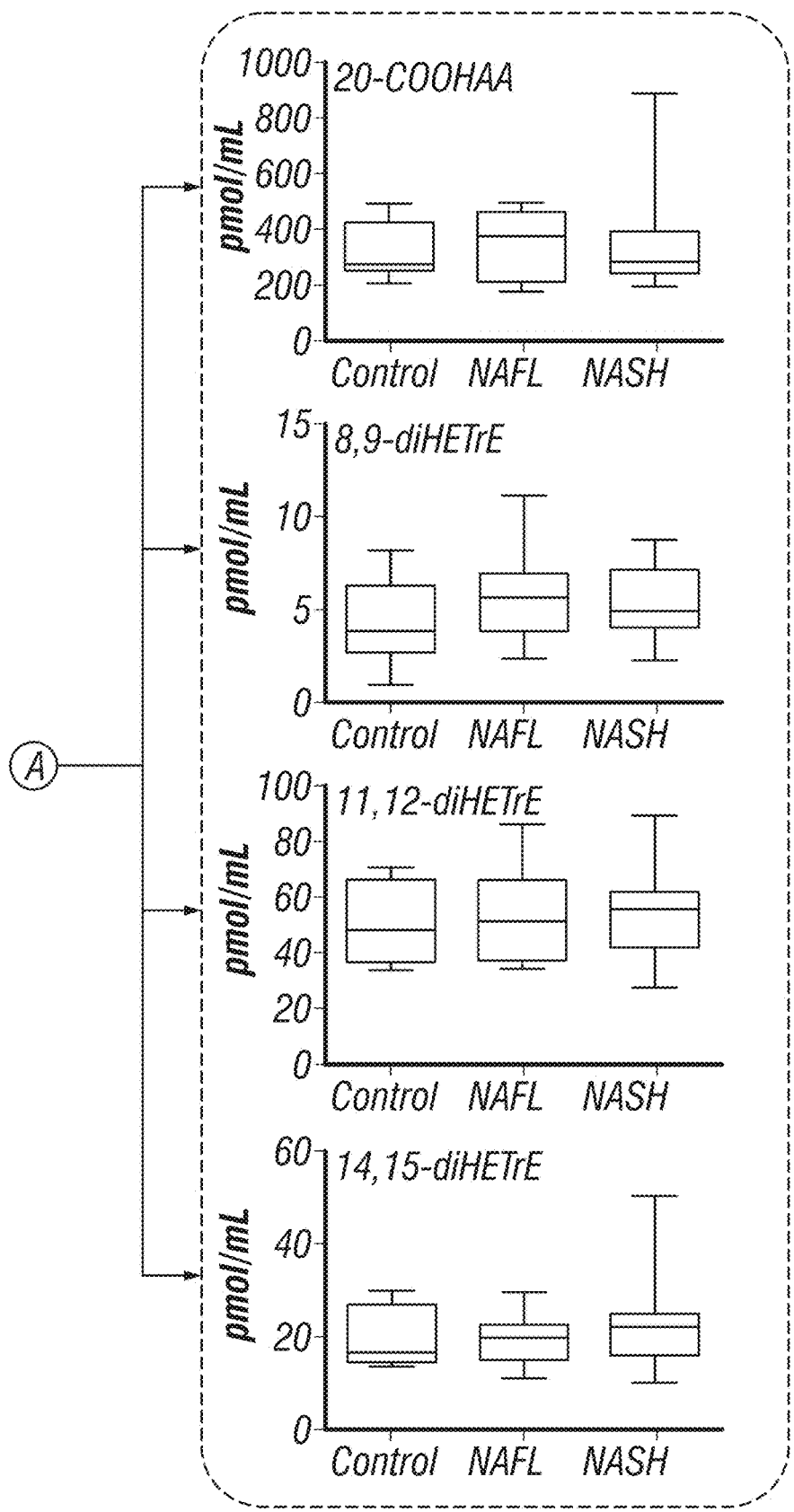
Figure 4:
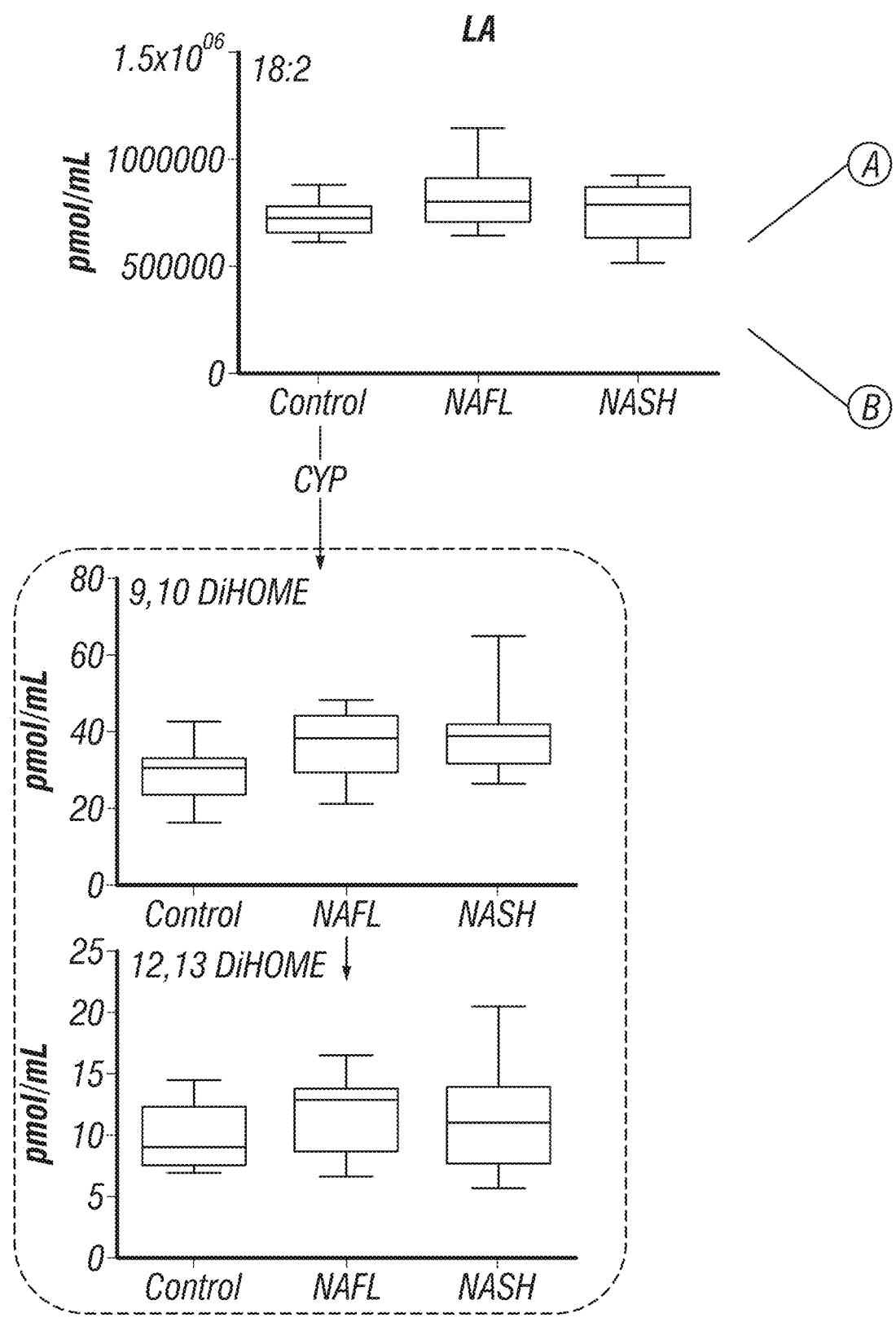
FIG. 4 shows the amounts of total linoleic acid (LA) and its metabolites derived from LOX, and CYP pathways in plasma in the three clinical arms for each metabolite.
Figure 4:
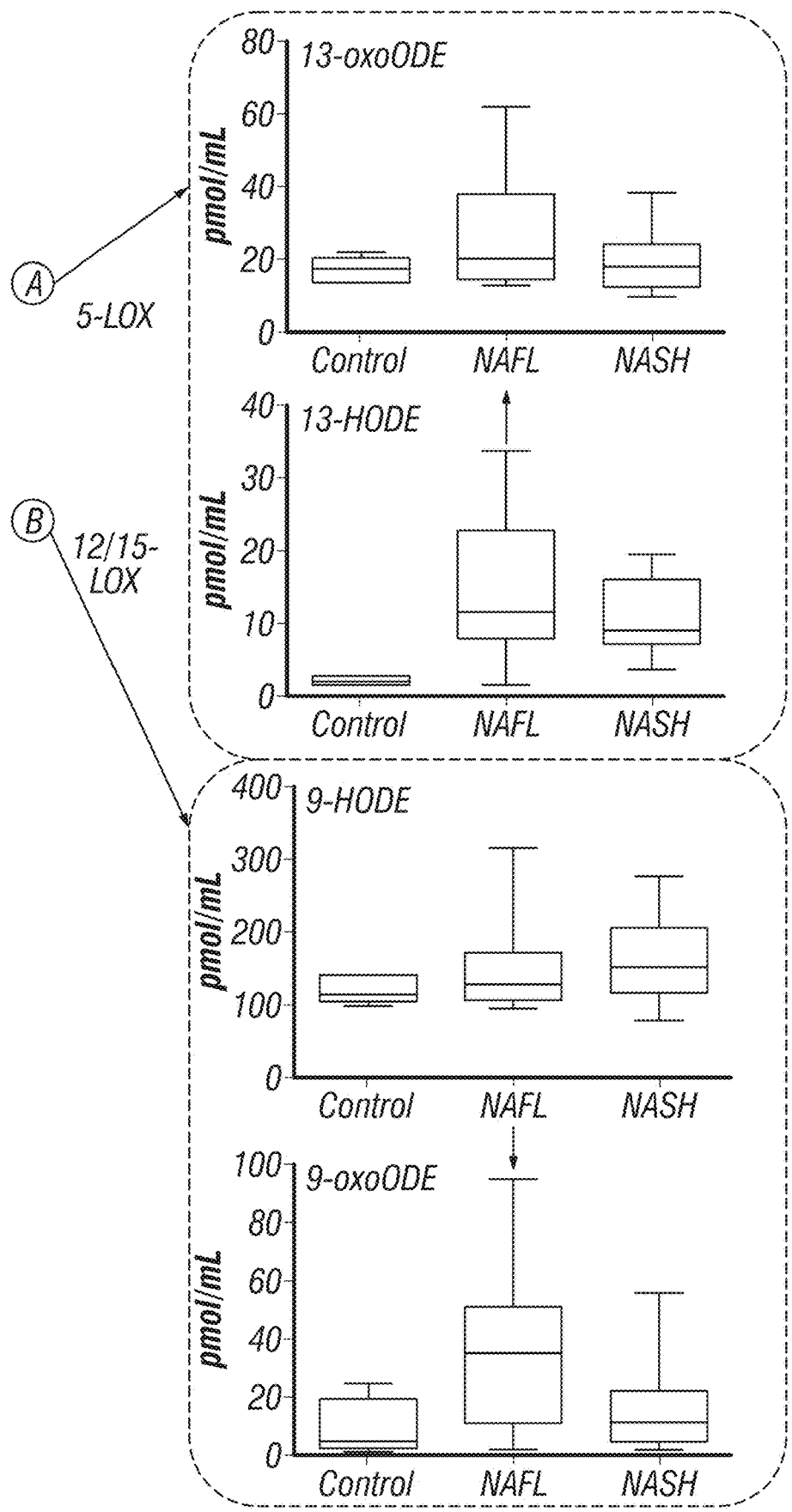
Figure 5:
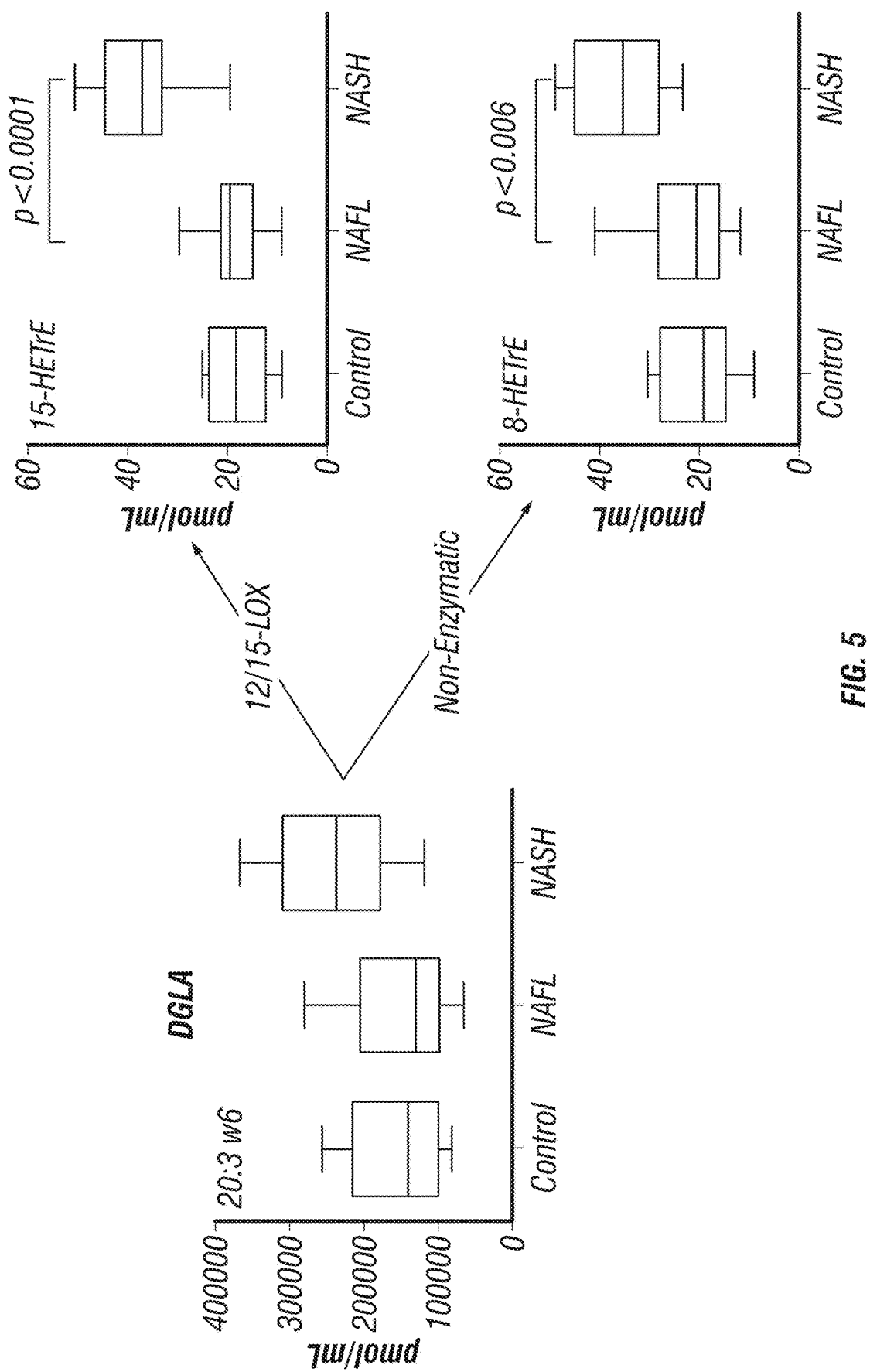
FIG. 5 shows the amounts of total dihomo-gamma-linolenic acid (DGLA) and its metabolites derived from LOX and non-enzymatic pathways in plasma in the three clinical arms for each metabolite. Differences between groups were evaluated with a Student's t-test and p values<0.05 are indicated.
Figure 6:
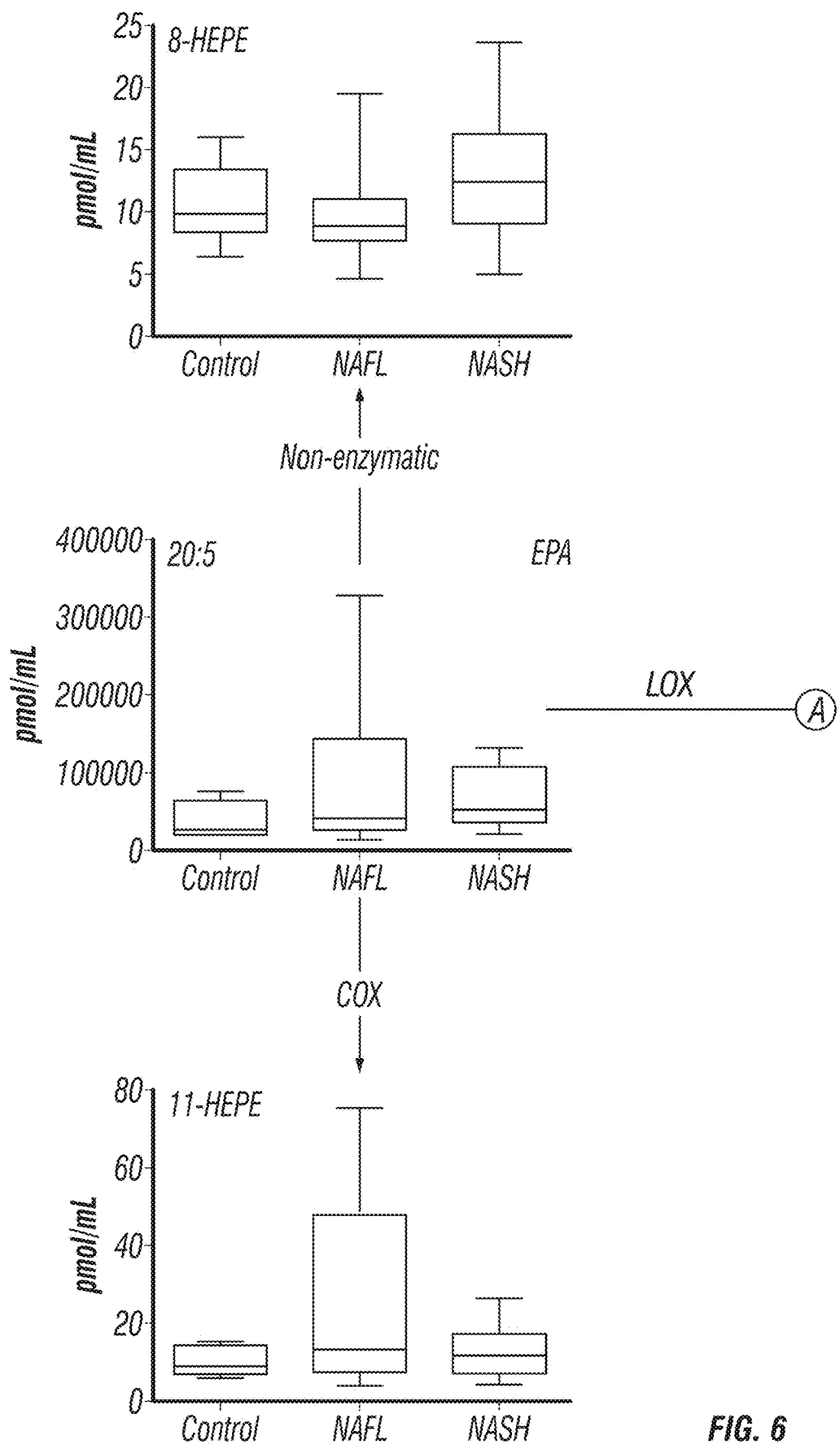
FIG. 6 shows the amounts of total eicosapentaenoic acid (EPA) and its metabolites derived from COX, LOX, and non-enzymatic pathways in plasma in the three clinical arms for each metabolite.
Figure 6:
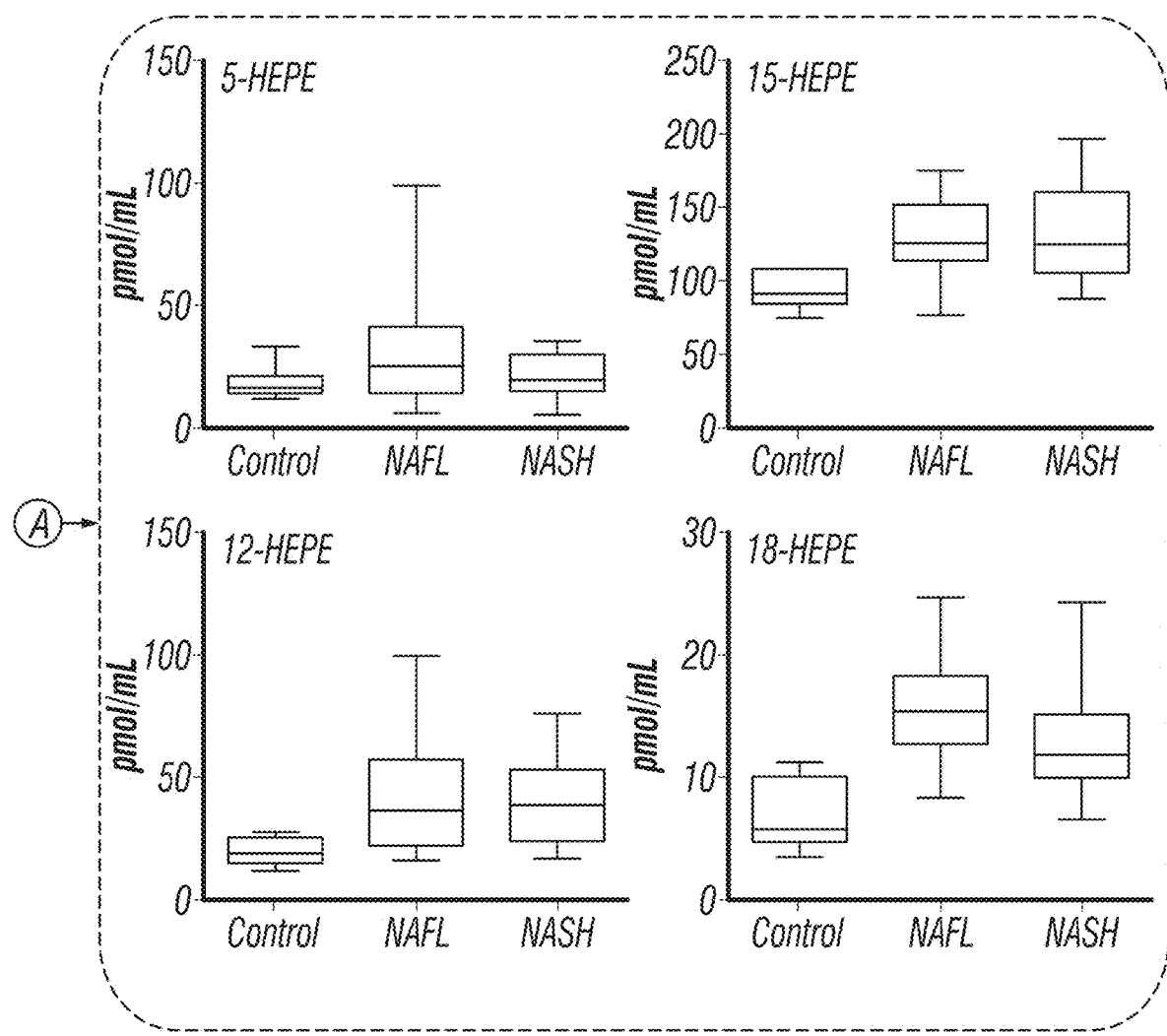
Figure 7:
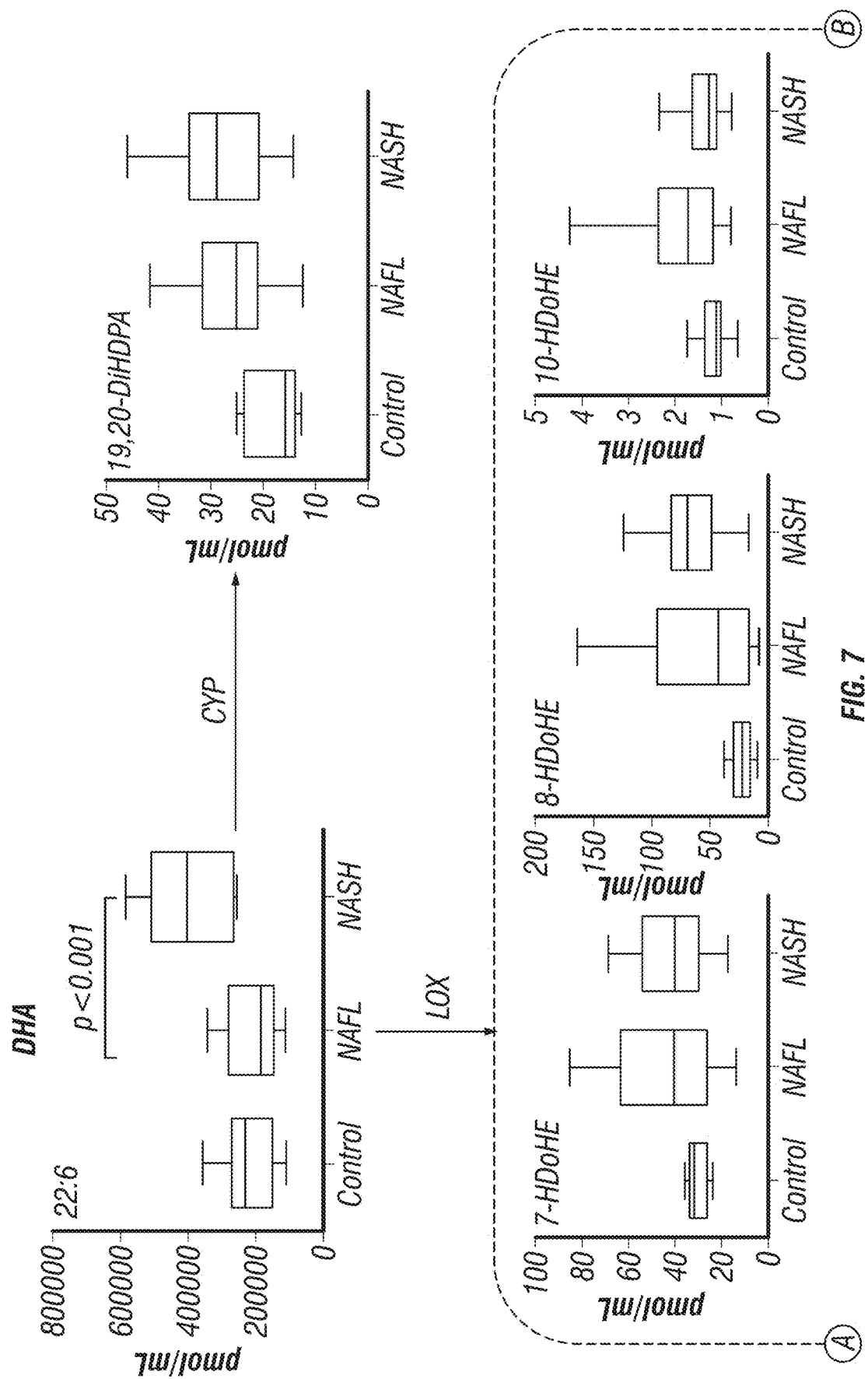
FIG. 7 shows the amounts of total docosahexaenoic acid (DHA) and its metabolites derived from LOX, and CYP pathways in plasma in the three clinical arms for each metabolite. Differences between groups were evaluated with a Student's t-test and p values<0.05 are indicated.
Figure 7:
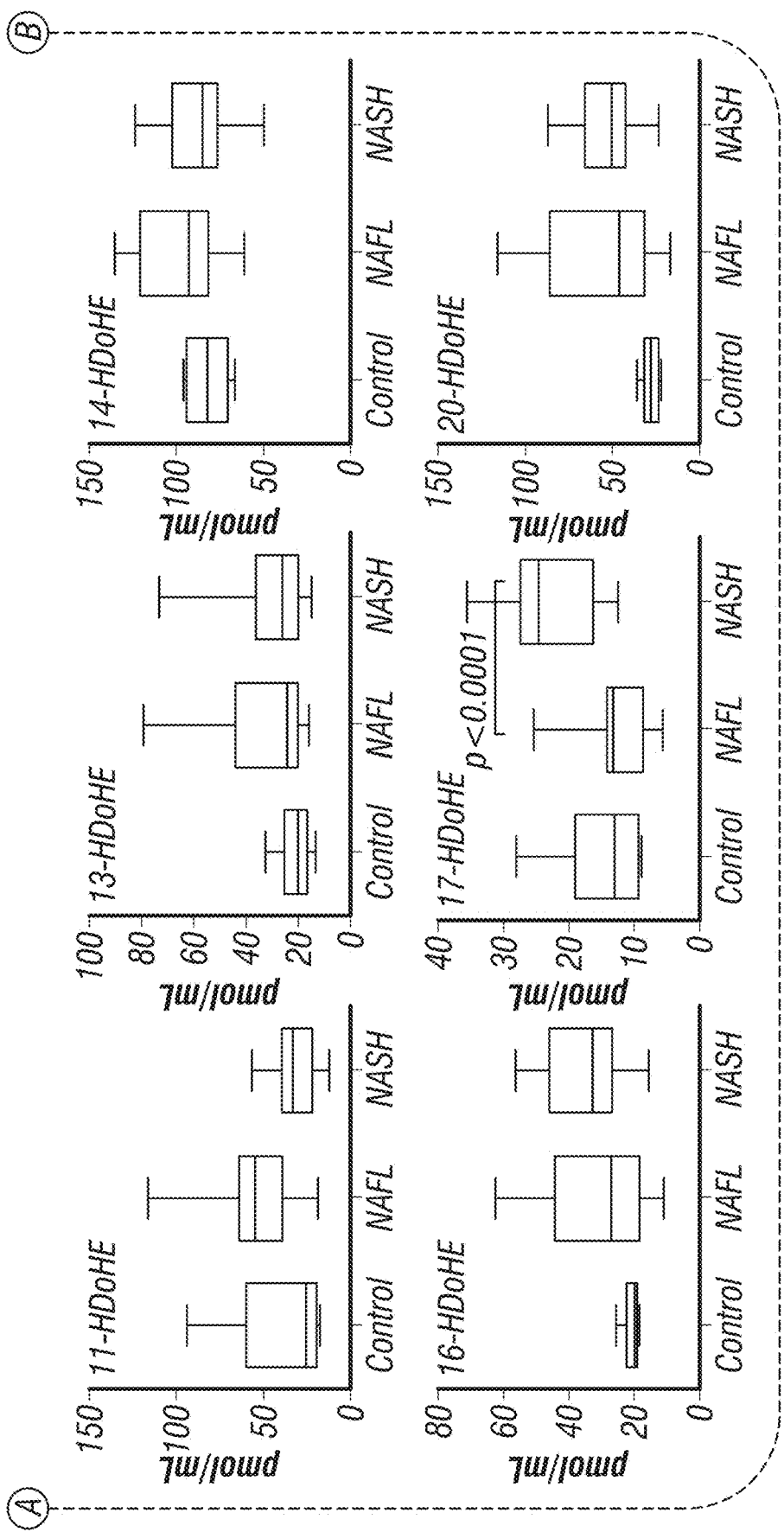

The metabolites derived from AA are displayed in FIG. 3 and show slightly increased levels in NAFL and NASH but these increases did not reach significance in this study. Similarly, 9,10-EpOME, 9,10-DIHOME, 13-HODE, and 9-oxoODE, all metabolites derived from linoleic acid (LA), showed stepwise increases in NAFL and NASH, compared with controls (FIG. 4). Clinically, it is important to be able to distinguish NAFL from NASH and several of these metabolites including 13-HODE and 9-oxoODE were present at higher levels in the plasma from NAFL compared with NASH. In addition, several metabolites derived from DGLA including 8-HETrE and 15-HETrE were also significantly increased in NASH, whereas no differences were found between control and NAFL (FIG. 5). Interestingly, the plasma levels of both the omega-3 fatty acid DHA and its anti-inflammatory metabolite 17-HDoHE were significantly increased in NASH (FIG. 7).

During the preliminary UPLC/MS/MS method development, different concentrations of KOH (0.33-1.31M) and BHT (0 to 10 mM) in the sample extract solution were compared. Based on the quality of peak shape and resolution of metabolites, it was confirmed that about 0.66 M KOH (e.g., about 0.62-0.70 M KOH) and about 2.5 mM BHT (e.g., about 2.0 to 3.0 mM BHT) in the lipid extraction solution yielded the optimal results. Higher base results in too much eicosanoid degradation, and lesser gives insufficient hydrolysis of esterified oxidized complex lipids. In one embodiment, the amount of KOH is 0.66M. Too high a BHT concentration produces crystallization. In another embodiment, the amount of BHT is 2.5 mM. During the process and prior to the SPE column, the extract was diluted with $H_2O$ to avoid too high a salt concentration during the SPE extract.

Generally, the internal standards were degraded, to some extent under alkaline hydrolysis conditions. Especially the polar eicosanoids (LTB4, LTC4, LTE4, PGE2, PGD2, PGJ2, 6k PGF1a, dhk PGF2a, 15d PGJ2) proved to be particularly susceptible to degradation. Unlike fatty acids, most naturally occurring prostaglandins have a considerable potential for hydrolysis, dehydration, or isomerization, depending on their immediate environment. Prostaglandins contain multiple hydroxyl groups, keto groups and a rigid 5-member prostane ring. The resulting β-hydroxy ketone system is unstable and readily undergoes dehydration under acidic or basic conditions to A-type prostaglandins, those containing a cyclopentenone ring such as prostaglandin A2. Under basic conditions, the A prostaglandins can isomerize further to B prostaglandins such as prostaglandin B. In strong alkaline solutions the formation of PGB2 is so rapid (within seconds with 0.5M KOH in 9:1 methanol-water). PGE lacking the 5, 6-double bond can be rapidly converted to essentially inactive PGB by treating with 0.1M base, while the formation of PGB was not observed in the study.

For the deuterated internal standards, the recovery after alkaline hydrolysis varied greatly, with some metabolites largely degraded and others fully recovered (Table 1). Generally, the recovery of the non-deuterated primary standards matched that of the deuterated internal standards (Table 2 and Table 3). These results indicate that the reduced recovery of the deuterated standards after exposure to alkaline conditions is not caused by a loss of a deuterium due to exchange reactions with hydrogen but is primarily a result of rearrangement of the molecular structure or degradation. Consistent with this hypothesis, the study shows that alkaline conditions actually increased the levels of several metabolites. For example, hydroxylated metabolites of AA including 16-HETE, 17-HETE, 18-HETE, 19-HETE and 20-HETE were increased (Table 3). These metabolites can be generated enzymatically via the CYP pathway or non-enzymatically as a result of autoxidation. The disclosure demonstrates that the saponification process which was applied to hydrolyze esterified oxidized fatty acids in the samples could induce some degradation or isomerization of deuterated and non-deuterated eicosanoids. In contrast, the fatty acids precursors of the eicosanoids and related oxidized PUFA are much more stable under alkaline conditions.

TABLE 3

Recovery of primary standards subjected to alkaline hydrolysis[1].

| No | Standard | Control (Intensity × $10^4$) | RSD (%) | Saponified (Intensity × $10^4$) | RSD (%) | Recovery (%) |
|---|---|---|---|---|---|---|
| | | COX Biosynthetic Pathway | | | | |
| 1 | 11-HEPE | 1,060 | 4.3 | 721 | 3.7 | 68 |
| 2 | 11-HETE | 3,060 | 3.4 | 2,160 | 1.5 | 71 |
| 3 | 12-HHTrE | 295 | 4.4 | 19 | 18 | 7 |
| 4 | PGA2 | 2,890 | 2.9 | 34 | 9.2 | 1 |
| 5 | 15d PGA2 | 12 | 11 | ND | 0 | 0 |
| 6 | PGB2 | 1,120 | 5.6 | ND | 0 | 0 |
| 7 | PGD1 | 90 | 6.5 | ND | 0 | 0 |
| 8 | PGD2 | 279 | 3.9 | ND | 0 | 0 |
| 9 | 15d PGD2 | 1,300 | 6.8 | ND | 0 | 0 |
| 10 | dhk PGD2 | 228 | 3.6 | ND | 0 | 0 |
| 11 | PGD3 | 89 | 3.9 | ND | 0 | 0 |
| 12 | tetranor-PGDM | 14 | 1.7 | 3.8 | 15 | 27 |
| 13 | PGE1 | 107 | 8.9 | ND | 0 | 0 |
| 14 | 6k PGE1 | 385 | 9.3 | ND | 0 | 0 |
| 15 | PGE2 | 437 | 13 | ND | 0 | 0 |
| 16 | 11b PGE2 | 402 | 7.2 | ND | 0 | 0 |
| 17 | bicyclo PGE2 | 274 | 5.9 | ND | 0 | 0 |
| 65 | 8-HEPE | 174 | 2.1 | 264 | 3.2 | 152 |
| 66 | 8,15-diHETE | 127 | 2.2 | 18 | 12 | 14 |
| 67 | 12-HEPE | 719 | 1.5 | 1,050 | 3.4 | 147 |
| 68 | 15-HEPE | 823 | 3.9 | 1,150 | 5.1 | 141 |
| 69 | 5-HETrE | 494 | 3.4 | 299 | 1.5 | 61 |
| 70 | 8-HETrE | 746 | 2.5 | 448 | 3.5 | 60 |
| 71 | 15-HETrE | 2,170 | 2.2 | 1,320 | 6.2 | 61 |
| 72 | 9-HODE | 1,200 | 2 | 524 | 11 | 44 |
| 73 | 13-HODE | 1,220 | 1.9 | 571 | 7.6 | 47 |
| 74 | 9-HOTrE | 567 | 1.8 | 329 | 7.5 | 58 |
| 75 | 13-HOTrE | 219 | 3.3 | 277 | 4.9 | 126 |
| 76 | 13-HOTrE(y) | 1,180 | 2.8 | 1,170 | 8.4 | 100 |
| 77 | HXA3 | 34 | 1.7 | 12 | 1.9 | 35 |
| 78 | HXB3 | 396 | 2.6 | 81 | 10 | 21 |
| 79 | LTB4 | 2,460 | 6.4 | 283 | 17 | 12 |
| 80 | 20oh LTB4 | 288 | 2.6 | 58 | 7.8 | 20 |
| 81 | 6t LTB4 | 2,660 | 7.6 | 322 | 15 | 12 |
| 82 | 12epi LTB4 | 2,650 | 7.1 | 316 | 14 | 12 |
| 83 | 6t,12epi LTB4 | 2,640 | 6.8 | 293 | 16 | 11 |
| 84 | 12oxo LTB4 | 2,630 | 6.1 | 291 | 19 | 11 |
| 85 | LTC4 | 1.1 | 78 | ND | 0 | 0 |
| 86 | 14,15 LTC4 | 172 | 7.1 | ND | 0 | 0 |
| 87 | 14,15 LTD4 | 30 | 68 | ND | 0 | 0 |
| 88 | 11t LTC4 | 0.3 | 70 | ND | 0 | 0 |
| 89 | LTD4 | 105 | 6.1 | ND | 0 | 0 |
| 90 | 11t LTD4 | 124 | 0.3 | ND | 0 | 0 |
| 91 | LTE4 | 139 | 0.5 | 12 | 28 | 9 |
| 92 | 11t LTE4 | 51 | 6.7 | 4.5 | 24 | 9 |
| 93 | 14,15 LTE4 | 48 | 3.3 | 1.6 | 49 | 3 |
| 94 | 6R-LXA4 | ND | 0 | ND | 0 | 0 |
| 95 | 6S-LXA4 | 225 | 8.9 | 12 | 9.4 | 6 |
| 96 | LXA5 | 2.3 | 12 | ND | 0 | 0 |
| 97 | LXB4 | 117 | 3.5 | 13 | 28 | 11 |
| 98 | 9-oxoODE | 261 | 3.6 | 134 | 8.9 | 52 |
| 99 | 13-oxoODE | 111 | 1.9 | 53 | 9.5 | 48 |
| 100 | 15oxoEDE | 365 | 5.7 | 160 | 8.7 | 44 |
| 101 | 10S-Protectin D1 | 0.9 | 7.9 | ND | 0 | 0 |
| 102 | Resolvin D1 | 232 | 11 | 27 | 17 | 12 |
| 103 | 20cooh LTB4 | 62.6 | 2.5 | 13 | 6.1 | 22 |
| 104 | 17 HDoHE | 55.6 | 3.8 | 34 | 2.3 | 62 |
| 105 | 17k DPA | 252 | 7.7 | 8.0 | 17 | 3 |
| | | CYP Biosynthetic Pathway | | | | |
| 106 | 20COOH AA | 709 | 0.0 | 1,100 | 2.1 | 156 |
| 107 | 9,10 EpOME | 1,000 | 4.7 | 159 | 14 | 16 |
| 108 | 12,13 EpOME | 1,170 | 4.7 | 170 | 14 | 15 |
| 109 | 16-HETE | 374 | 2.2 | 472 | 2.3 | 127 |
| 110 | 17-HETE | 1420 | 2.0 | 1,790 | 2.5 | 126 |
| 111 | 18-HETE | 1020 | 1.4 | 1,430 | 3.6 | 140 |
| 112 | 19-HETE | 206 | 3.4 | 267 | 2.6 | 130 |
| 113 | 20-HETE | 175 | 2.7 | 229 | 2.7 | 131 |
| 114 | 18-HEPE | 1040 | 3.2 | 631 | 5.1 | 60 |
| 115 | 5,15-diHETE | 337 | 2.0 | 71 | 12 | 21 |
| 116 | 19,20 DiHDPA | 398 | 1.5 | 276 | 0.1 | 69 |
| 117 | 5,6-diHETrE | 589 | 3.2 | 1,760 | 0.3 | 299 |
| 118 | 8,9-diHETrE | 418 | 0.4 | 319 | 0.1 | 76 |

TABLE 3-continued

Recovery of primary standards subjected to alkaline hydrolysis[1].

| No | Standard | Control (Intensity × 10^4) | RSD (%) | Saponified (Intensity × 10^4) | RSD (%) | Recovery (%) |
|---|---|---|---|---|---|---|
| 119 | 11,12-diHETrE | 1,820 | 4.4 | 1,259 | 1.8 | 69 |
| 120 | 14,15-diHETrE | 2,100 | 3.7 | 1,510 | 0.2 | 72 |
| 121 | 9,10 diHOME | 2,120 | 4.6 | 1,410 | 0.3 | 67 |
| 122 | 12,13 diHOME | 1,830 | 4.5 | 1,400 | 0.1 | 77 |
| 123 | 5,6-EET | 206.1 | 5.6 | 25 | 14 | 13 |
| 124 | 8,9-EET | 224.0 | 6.3 | 79 | 7.4 | 36 |
| 125 | 11,12-EET | 840.1 | 9.9 | 286 | 3.4 | 34 |
| 126 | 14,15-EET | 219.5 | 7.2 | 44 | 10 | 20 |
| 127 | 14(15) EpETE | 481.0 | 6.2 | 291 | 2.1 | 61 |
| 128 | 17(18) EpETE | 245.8 | 3.3 | 44 | 12 | 18 |
| 129 | 16(17) EpDPE | 106.6 | 0.5 | 45 | 7.3 | 43 |
| 130 | 19(20) EpDPE | 407.3 | 5.5 | 116 | 1.2 | 29 |
| | Non-enzymatic Pathway | | | | | |
| 131 | 4 HDoHE | 299.9 | 4.8 | 170 | 3.2 | 57 |
| 132 | 7 HDoHE | 332.5 | 2.8 | 200 | 4.0 | 60 |
| 133 | 8 HDoHE | 153.1 | 8.2 | 88 | 6.1 | 58 |
| 134 | 10 HDoHE | 833.3 | 4.7 | 525 | 1.5 | 63 |
| 135 | 11 HDoHE | 577.1 | 5.3 | 349 | 2.9 | 61 |
| 136 | 14 HDoHE | 322.4 | 2.9 | 216 | 3.2 | 67 |
| 137 | 16 HDoHE | 1,310 | 3.7 | 809 | 2.1 | 62 |
| 138 | 20 HDoHE | 529.6 | 2.3 | 309 | 5.2 | 58 |
| 139 | 9-HEPE | 474.5 | 3.7 | 661 | 5.7 | 140 |
| 140 | 9-HETE | 171.8 | 1.9 | 120 | 3.0 | 70 |
| 141 | 9-Nitrooleate | 40.9 | 6.4 | ND | 0.0 | 0 |
| 142 | 10-Nitrooleate | 19 | 7.0 | ND | 0.0 | 0 |
| 143 | 7(R) Maresin-1 | 179 | 4.7 | ND | 0.0 | 0 |
| 144 | 5-iso PGF2a VI | 97 | 2.8 | 32 | 0.5 | 34 |
| 145 | 8-iso PGF2a III | 181 | 4.0 | 89 | 0.4 | 49 |
| 146 | 2,3 dinor 8-iso PGF2a | 587 | 1.3 | 325 | 5.4 | 55 |
| 147 | 8-iso-15k PGF2b | 90 | 6.3 | ND | 0.0 | 0 |
| 148 | 8-iso PGF3a | 193 | 6.7 | 85 | 9.5 | 44 |

[1]ND means non-detectable, indicating a peak with a single-to-noise ratio (S/N) lower than 3:1.
RSD is the relative standard deviation.

The principal findings from the NAFLD samples relate to the identification of specific fatty acid oxidation products as potential novel, systemic, noninvasive markers to differentiate NASH from NAFL. The concentrations of LA, AA, DGLA, EPA and DHA derivatives from enzymatic and free radical pathways in the plasma of patients with NAFLD and healthy individuals were evaluated. Most of the literature addresses oxidative stress as a core abnormality responsible for disease progression and NAFLD; however, the pathways contributing to oxidative damage in vivo are poorly understood.

Many of the PUFA products are much more elevated in NAFL and NASH subjects compared to control (FIG. 3-FIG. 7). Lipid peroxidation products such as HODEs originating from the conversion of LA and HETEs originating from the conversion of AA in reactions catalyzed by cellular lipoxygenases were increased in the liver during peroxidation in association with the increase in triglyceride. The plasma concentrations of proinflammatory eicosanoids including 5-HETE, 8-HETE, 11-HETE, 15-HETE, 13-HODE, and 9-oxoODE are much more elevated in NAFL patients compared to NASH patients and control subjects (FIG. 3, FIG. 4). The decrease in NASH indicated some of the eicosanoids were degraded into others. Feldstein et al. characterized an increase in HODEs and oxoODEs from fatty liver to steatohepatitis (J. Lipid Res., 51:3046-3054, 2010). Using the algorithm defined as a recovery >60%, these metabolites did not satisfy the criteria for recovery (Table 4 and Table 3) and, thus, were excluded from further analysis. The approach using the optimized saponification procedure and applying the metabolite inclusion/exclusion algorithm led to the identification of metabolites, specifically 8-HETrE and 15-HETrE, which were significantly elevated in NASH compared with NAFL (p<0.001). Using plasma from the same patient and control pool, both free and total 15-HETrE was significantly enhanced in the NASH stage of the disease compared with NAFL and control. As can be seen in FIG. 5, 8-HETrE followed the same trend.

Interestingly, the omega-3 fatty acid DHA (p<0.001) and its metabolite 17-HDoHE (p<0.0001), were significantly increased in NASH compared with NAFL and control (FIG. 7). The latter metabolite is of particular interest as it is a precursor for protectins, a group of lipid mediators with anti-inflammatory properties.

TABLE 4

Primary standards recovered at ≥60% after alkaline hydrolysis.

| Pathway | Metabolites | Recovery (%) |
|---|---|---|
| COX | 11-HEPE | 68 |
| | 11-HETE | 71 |
| | dh PGF2a | 66 |
| | PGK1 | 228 |
| | 11d-TXB2 | 100 |
| LOX | 13 HDoHE | 65 |
| | 5,6-diHETE | 101 |
| | 8-HETE | 70 |
| | 12-HETE | 72 |
| | 15-HETE | 63 |
| | 5-HEPE | 75 |
| | 8-HEPE | 152 |

TABLE 4-continued

Primary standards recovered at ≥60% after alkaline hydrolysis.

| Pathway | Metabolites | Recovery (%) |
|---|---|---|
| CYP | 12-HEPE | 147 |
| | 15-HEPE | 141 |
| | 5-HETrE | 61 |
| | 8-HETrE | 60 |
| | 15-HETrE | 61 |
| | 13-HOTrE | 126 |
| | 13-HOTrE(y) | 100 |
| | 20COOH AA | 156 |
| | 16-HETE | 127 |
| | 17-HETE | 126 |
| | 18-HETE | 140 |
| | 19-HETE | 130 |
| | 20-HETE | 131 |
| | 18-HEPE | 60 |
| | 19,20 DiHDPA | 69 |
| | 5,6-diHETrE | 299 |
| | 8,9-diHETrE | 76 |
| | 11,12-diHETrE | 69 |
| | 14,15-diHETrE | 72 |
| | 9,10 diHOME | 67 |
| | 12,13 diHOME | 77 |
| | 14(15) EpETE | 61 |
| Non-enzymatic | 7 HDoHE | 60 |
| | 10 HDoHE | 63 |
| | 11 HDoHE | 61 |
| | 14 HDoHE | 67 |
| | 16 HDoHE | 62 |
| | 17 HDoHE | 62 |
| | 9-HEPE | 140 |
| | 9-HETE | 70 |

Numerous modifications and variations in the invention as set forth in the above illustrative examples are expected to occur to those skilled in the art. Consequently only such limitations as appear in the appended claims should be placed on the invention.

What is claimed:

1. A method of differentiating nonalcoholic steatohepatitis (NASH) from nonalcoholic fatty liver (NAFL) in a subject, comprising:
   (a) obtaining a biological sample from the subject;
   (b) treating the sample with 0.6-0.7M KOH to release esterified eicosanoids and recovering the eicosanoids and polyunsaturated fatty acids (PUFAs);
   (c) measuring the level of (i) 8-HETrE; (ii) 15-HETrE, (iii) omega-3 fatty acid DHA, and (iv) 17-HDoHE, and optionally one or more additional eicosanoids and/or PUFAs selected from the group consisting of 5-HETE, 8-HETE, 11-HETE, 15-HETE, 13-NODE, and 9-oxoODE;
   (d) expressing the levels of the eicosanoids and PUFAs as the area under receiver operating characteristic curve (AUROC) based upon a ratio of the levels of the eicosanoid and/or PUFAs matched with deuterated internal standards of the same metabolite; and
   (e) comparing the expressed levels of eicosanoid and PUFAs to a control sample obtained from a NAFL subject, wherein a difference in the expressed levels of the eicosanoid and PUFAs of at least 0.8 in the sample obtained from the subject compared to the control is indicative of NASH.

2. The method of claim 1, wherein the eicosanoids obtained from (b) are eicosanoids recovered at greater than 60%.

3. The method of claim 1, wherein the biological sample is selected from the group consisting of blood, blood plasma and blood serum.

4. The method of claim 1, further comprising adding butylated hydroxytoluene (BHT) prior to alkaline treatment.

5. The method of claim 4, wherein about 2.5 mM BHT is used.

6. The method of claim 1, wherein the eicosanoids are measured by liquid chromatography.

7. The method of claim 1, wherein fatty acids are measured by gas chromatography mass spectrometry.

* * * * *